United States Patent [19]

Woodward

[11] Patent Number: 5,011,856

[45] Date of Patent: Apr. 30, 1991

[54] USE OF PROSTAGLANDIN F3 ALPHA AS AN OCULAR HYPOTENSIVE AGENT

[75] Inventor: David A. Woodward, El Toro, Calif.

[73] Assignee: Allergan, Inc., Irvine, Calif.

[21] Appl. No.: 491,546

[22] Filed: Mar. 12, 1990

[51] Int. Cl.$^5$ ............... A61K 31/557; A61K 31/215; A01N 37/08; C07C 405/00

[52] U.S. Cl. .................................. 514/573; 514/530; 514/912; 514/913; 424/427

[58] Field of Search ............... 424/427; 514/530, 573, 514/912, 913

[56] References Cited

U.S. PATENT DOCUMENTS

| | | | |
|---|---|---|---|
| 3,853,854 | 12/1974 | Weinshenker et al. | 549/415 |
| 3,940,438 | 2/1976 | Weinshenker | 562/503 |
| 3,941,886 | 3/1976 | Weinshenker | 514/573 |
| 4,001,306 | 1/1977 | Morozowich et al. | 560/231 |
| 4,016,184 | 4/1977 | Morton, Jr. | 260/408 |
| 4,033,989 | 7/1977 | Bundy | 260/408 |
| 4,049,678 | 9/1977 | Peterson | 549/267 |
| 4,055,593 | 10/1977 | Weinshenker et al. | 562/503 |
| 4,060,540 | 11/1977 | Barnady et al. | 556/441 |
| 4,099,014 | 7/1978 | Peterson | 562/463 |
| 4,149,007 | 4/1979 | Buckler et al. | 514/822 |
| 4,599,353 | 7/1986 | Bito | 514/530 |
| 4,822,819 | 4/1989 | DeSantis et al. | 514/530 |
| 4,824,857 | 4/1989 | Goh et al. | 514/398 |
| 4,883,819 | 11/1989 | Bito | 514/573 |

FOREIGN PATENT DOCUMENTS

| | | |
|---|---|---|
| 0286903 | 4/1987 | European Pat. Off. . |
| 8806448 | 9/1988 | PCT Int'l Appl. . |
| 8903384 | 4/1989 | PCT Int'l Appl. . |

OTHER PUBLICATIONS

Andersen, Neils *Prostaglandin* 6(5):361–374 (1974).
Bito, *Arch. Ophthalmol.* 105 (1987).
Camras et al., *Invest. Ophthalmol. Vis. Sci.* 16, 1125 (1977).
Gandolfo, C. et al., *Farmaco Ed. Sci.* 27:1125–1129 (1972).
Jenny, Erwin and Schaublin, Peter *Tetrahedron Letters* 26:2235–2238 (1974).
Keun Kim, *Investigative Ophthalmology* 14, 36 (1975).
Kondo, Kiyosi et al., *Tetrahedron Letters* 41:3927–3930 (1978).
Nilsson et al., *Exp. Eye Res.* 48, 707 (1989).
Siebold et al., *Prodrug* 5, 3 (1989).
Starr, *Exp. Eye Res.* 11, 170–177 (1971).
Zajacz et al., *The Eye: Reproduction, Obstetrics and Gynecology* 4, 316 (1976), Chem., Biochem., Pharmacol. Act Prostanoids, INCL. Proc. Symp., Meeting Date 1978, pp. 185–193, ed. Roberts, Stanley, N. and Scheinman, Theodore, Pergamon Press (1979).

*Primary Examiner*—Thurman K. Page
*Assistant Examiner*—Carlos Azpuru
*Attorney, Agent, or Firm*—Knobbe, Martens, Olson & Bear

[57] ABSTRACT

The invention relates to a means of reducing or maintaining intraocular pressure, and, more particularly, to a method and composition for reducing or maintaining intraocular pressure involving the administration of a composition containing prostaglandin F$_{3\alpha}$ in a pharmaceutically acceptable carrier.

3 Claims, No Drawings

USE OF PROSTAGLANDIN F3 ALPHA AS AN OCULAR HYPOTENSIVE AGENT

FIELD OF THE INVENTION

The present invention relates to a means of reducing or maintaining intraocular pressure, and, more particularly, to a method and composition for reducing or maintaining intraocular pressure involving the administration of a composition containing prostaglandin $F_{3\alpha}$ in a pharmaceutically acceptable carrier.

BACKGROUND OF THE INVENTION

The compositions and method of the present invention are particularly useful for the management of glaucoma, a disease of the eye characterized by increased intraocular pressure.

On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic openangle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivative include numerous biologically important compounds such as prostaglandins and their derivatives. Prostaglandins can be described as derivatives of prostanoic acid which has the following structural formula:

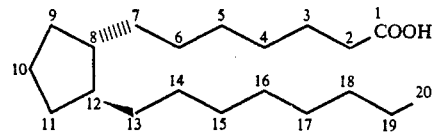

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection With Prostaglandins* Cohen, M. M., ed., Boca Raton, Fla., CRC Press Inc., 1985, pp. 231-252; and Bito, L. Z., *Applied Pharmacology in the Medical Treatment of Glaucomas* Drance, S. M. and Neufeld, A. H. eds., New York, Grune & Stratton, 1984, pp. 477-505). Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known, recent experimental results indicate that the prostaglandin-induced reduction in intraocular pressure results from increased oveoscleral outflow [Nilsson et al., *Invest. ophthalmol. Vis. Sci.* 28 (suppl), 284 (1987)].

The isopropyl ester of $PGF_{2\alpha}$ has been shown to have significantly greater hypotensive potency than the parent compound, presumably as a result of its more effective transfer through the cornea. In 1987 this compound was described as "the most potent ocular hypotensive agent ever reported" [see, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 July 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15- 9,15-and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312 and 386,834 (all filed 27 July 1989). The disclosures of all of these patent applications are hereby expressly incorporated by reference.

SUMMARY OF THE INVENTION

The present invention relates to the use of prostaglandin $F_{3\alpha}$, formulated in a pharmaceutically acceptable vehicle, for the treatment of glaucoma and ocular hypertension. The present invention is based on the surprising discovery that the aforementioned undesirable side effects are entirely absent or at least, are substantially reduced when $PGF_{3\alpha}$. The separation of intraocular pressure-reducing and ocular surface hyperemiacausing properties is unexpected in the case of an unesterified PG compound.

In accordance with another aspect of the present invention, there is provided a topically applicable pharmaceutical composition for treating ocular hypertension which comprises prostaglandin $F_{3\alpha}$ of the formula (I)

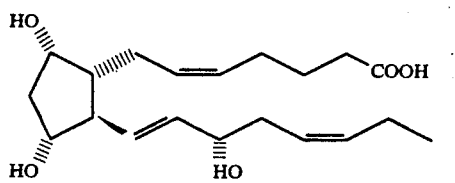

or a salt thereof present in a pharmaceutically acceptable excipient, in a therapeutically effective amount. The therapeutically effective amount usually is within the range of approximately 0.0001% to 5%. Optionally, the composition of the present invention may further comprise co-solvents, pH buffers, viscosity enhancers, antibiotics or other advantageous adjuvants.

In accordance with a further aspect of the present invention, there is provided a method of treating ocular hypertension which comprises administering to a mammal having ocular hypertension a therapeutically effective amount of prostaglandin $PGF_{3\alpha}$; or a pharmaceutically acceptable salt thereof.

In a further aspect, the present invention relates to an ophthalmic solution comprising a therapeutically effective amount of $PGF_{3\alpha}$, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising a container adapted to dispense its contents in metered form; and an ophthalmic solution therein, as hereinabove defined.

Further features and advantages of the present invention will become apparent from the detailed description of preferred embodiments which follows, taken together with the examples and claims appended hereto.

DETAILED DESCRIPTION OF THE INVENTION

The present invention relates to the use of $PGF_{3\alpha}$ and pharmaceutically acceptable salts thereof as ocular hypotensives. $PGF_{3\alpha}$ has the following structural formula (I)

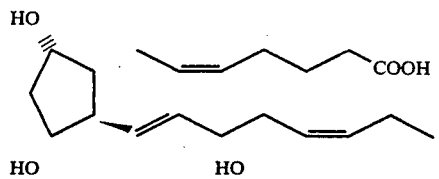

In the foregoing formula thickened solid line attachment indicates the beta configuration. The broken line attachments of the hydroxyl groups indicate that these substituents are in alpha configuration.

As hereinabove mentioned, it has been established that $PGF_{2\alpha}$ lowers intraocular pressure in man and other mammals when applied topically to the eye. However, topical application of prostaglandin $F_{2\alpha}$ produces side effects such as conjunctival hyperemia, smarting, and foreign body sensations which range in degree from undesirable to unacceptable, depending upon the particular patient and the dosage necessary to produce a sufficient pressure regulating effect In addition, prostaglandin $F_{2\alpha}$ may produce transient ocular hypertension.

In accordance with the present invention, there has been provided an ocular hypotensive which comprises prostaglandin $F_{3\alpha}$. Quite surprisingly, prostaglandin $F_3$, which contains a 17-18 cis double bond, has greater ocular hypotensive activity than prostaglandin $F_{2\alpha}$ with significantly reduced adverse side effects, notably ocular surface hyperemia. Prostaglandin $F_{3\alpha}$ is, therefore, an excellent candidate for therapeutic treatment of a variety of ocular hypertensive conditions such as open-angle glaucoma, closed-angle glaucoma, ocular hypertensive episodes, post-surgical and post-laser trabeculectomy, and as a presurgical adjuvant The $PGF_{3\alpha}$ compound illustrated in Formula (I) is in the free acid form. However, as will be appreciated by one of skill in the art, any of a variety of the corresponding salts may also be utilized in the ophthalmic formulations of the present invention. Thus, if the carboxylic acid group at C-1 on any of the Formula (I) is designated:

A may be —OH to produce the free acid, or —OR where R may be either the anion component of any of a variety of pharmaceutically acceptable salts. A pharmaceutically acceptable salt is any salt which retains the activity of the parent compound and does not impart any deleterious or undesirable effect on the subject to which it is administered and in the context in which it is administered.

Suitable pharmaceutically acceptable salts may be derived from either an organic or inorganic base. Such a salt may comprise a mono- or polyvalent ion. Of particular interest are inorganic cations such as sodium, potassium, calcium, magnesium and zinc. Organic salts may be made with amines, particularly ammonium salts such as mono-, di- and trialkyl amines or ethanol amines. Salts may also be formed with caffeine, tromethamine and similar molecules. Where acid addition salts are formed from amines, any inorganic or organic acid may be used. Preferred salts are hydrogen chloride salts, sulfate salts, phosphate salts and salts of simple organic acids of 2 to 6 carbons, either the mono- or diacids. Quaternary ammonium compounds can be prepared from alkylating agents such as methyl iodide and the like.

Pharmaceutical compositions may be prepared by combining a therapeutically efficient amount of $PGF_{3\alpha}$ or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 0.1% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives and stabilizers.

Preferred preservatives that may be used in the pharmaceutical compositions of the present invention include, but are not limited to, benzalkonium chloride, chlorobutanol, thimerosal, phenylmercuric acetate and phenylmercuric nitrate. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable opthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 μl solution.

The invention can be more fully appreciated by the following example.

EXAMPLE

Experimental quantities of prostaglandin $F_{3\alpha}$ and prostaglandin $F_{2\alpha}$ were prepared by dissolution in 2% (w/v) $Na_2CO_3$ with the pH adjusted to 7.0 by 0.1N HCl. Experimental rabbits were treated by giving one drop to the ocular surface of either a 0.01%, 0.1% or 1% solution so that three treatment groups, each comprising 4–8 animals, were obtained for both prostaglandin $F_{3\alpha}$ and prostaglandin $F_{2\alpha}$. Intraocular pressure was measured by applanation pneumatonometry at the time of administration and at 0.5, 2, 3, 4, and 6 hours thereafter. Ocular surface hyperemia was visually assessed and described as either absent or present in some degree. The following data were obtained.

| | | INTRAOCULAR PRESSURE (mmHg) CHANGES AT PREDETERMINED TIMES (HR) AFTER PROSTAGLANDIN ADMINISTRATION CHANGES IN INTRAOCULAR PRESSURE (mmHg) AT PREDETERMINED TIMES (HR) | | | | |
|---|---|---|---|---|---|---|
| PROSTAGLANDIN | (DOSE %) | 1.0 | 2.0 | 3.0 | 4.0 | 6.0 |
| Prostaglandin $F_{3\alpha}$ | 0.01% | −3.7 | −7.7** | −5.5 | −4.3 | −0.3 |
| Prostaglandin $F_{3\alpha}$ | 0.1% | −8.9** | −9.3** | −6.8** | −5.0** | −2.7** |
| Prostaglandin $F_{3\alpha}$ | 1.0% | +4.0 | −9.0** | −8.9** | −12.6** | −10.0** |
| Prostaglandin $F_{2\alpha}$ | 0.01% | −1.25 | −2.6* | −1.3 | −1.25 | −0.3 |
| Prostaglandin $F_{2\alpha}$ | 0.1% | −1.25 | −5.0** | −2.1* | −2.9** | +0.9 |
| Prostaglandin $F_{2\alpha}$ | 1.0% | +10.2** | +3.75** | +2.0 | −2.0 | — |
| | | PERCENT ANIMALS EXHIBITING OCULAR SURFACE HYPEREMIA % HYPEREMIA AT PREDETERMINED TIMES (HR) | | | | |
| PROSTAGLANDIN | (DOSE %) | 1.0 | 2.0 | 3.0 | 4.0 | 6.0 |
| Prostaglandin $F_{3\alpha}$ | 0.01% | 67 | 12 | 0 | 0 | 0 |
| Prostaglandin $F_{3\alpha}$ | 0.1% | 100 | 100 | 40 | 20 | 20 |
| Prostaglandin $F_{3\alpha}$ | 1.0% | 100 | 100 | 100 | 80 | 20 |
| Prostaglandin $F_{2\alpha}$ | 0.01% | 100 | 66 | 25 | 50 | 12.5 |
| Prostaglandin $F_{2\alpha}$ | 0.1% | 100 | 100 | 100 | 100 | 100 |

| | -continued | | | | | |
|---|---|---|---|---|---|---|
| Prostaglandin $F_{2\alpha}$ | 1.0% | 100 | 100 | 100 | 100 | — |

\*$p < 0.05$,
\*\*$p < 0.01$ according to Students paired t test

Comparison of the data obtained with prostaglandin $F_{3\alpha}$ and prostaglandin $F_{2\alpha}$ indicates that prostaglandin $F_{3\alpha}$ is greater than 10 times more potent as an ocular hypotensive agent. Moreover, prostaglandin $F_{2\alpha}$ induced ocular hypotension is achieved with a very high incidence of ocular surface hyperemia, whereas for all doses of prostaglandin $F_{3\alpha}$ profound ocular hypotension could be achieved with a minimal incidence of ocular surface hyperemia. In addition, on a dose-effect basis, prostaglandin $F_{3\alpha}$ is much less potent in causing ocular hypertension, an effect which is considered undesirable in glaucoma therapy.

Although this invention is described herein in terms of certain preferred embodiments, these embodiments are intended to illustrate the invention and not to impose limits. Other embodiments that are apparent to those of skill in the art are also within the scope of this invention. Accordingly, the scope of this invention is intended to be defined only by reference to the appended claims.

What is claimed is:

1. A method of treating ocular hypertension which comprises administering to a mammal having ocular hypertension a therapeutically effective amount of $PGF_{3\alpha}$ or a pharmaceutically acceptable salt thereof.

2. The method of claim 1 wherein said compound is $PGF_{3\alpha}$.

3. An ophthalmic solution comprising a therapeutically effective amount of $PGF_{3\alpha}$ or a pharmaceutically acceptable salt thereof, in admixture with a non-toxic, ophthalmically acceptable liquid vehicle packaged in a container suitable for metered application.

* * * * *